United States Patent [19]
Santini

[11] 4,413,779
[45] Nov. 8, 1983

[54] VAPOR DISPERSING DEVICE

[75] Inventor: Thomas F. Santini, New York, N.Y.

[73] Assignee: De Laire, Inc., New York, N.Y.

[21] Appl. No.: 259,068

[22] Filed: Apr. 30, 1981

Related U.S. Application Data

[63] Continuation-in-part of Ser. No. 246,089, Mar. 23, 1981, abandoned.

[51] Int. Cl.$^3$ ............................ A61L 9/04; A61L 9/12
[52] U.S. Cl. ........................................ 239/45; 239/44; 239/49; 422/4; 422/123; 422/306; 424/19
[58] Field of Search ........................... 422/4, 123, 306; 239/45, 49, 58, 44; 424/19, 76

[56] References Cited

U.S. PATENT DOCUMENTS

| 152,519 | 6/1874 | Sanborn | 239/50 |
| 1,129,897 | 3/1915 | Owen | 239/50 X |
| 1,358,928 | 11/1920 | Boehm | 239/58 |
| 2,616,759 | 11/1952 | Walsh | 239/47 |
| 2,787,496 | 4/1957 | Skaist | 239/45 |
| 2,975,464 | 3/1961 | Schultz | 239/44 X |
| 3,482,929 | 12/1969 | Gentil | 422/4 |
| 3,550,853 | 12/1970 | Gray | 239/44 |
| 3,595,607 | 7/1971 | Gones | 422/123 |
| 3,820,308 | 6/1974 | Onuki | 422/4 X |
| 4,094,639 | 6/1978 | McMillan | 239/58 |

FOREIGN PATENT DOCUMENTS

| 21586 | 1/1981 | European Pat. Off. | 422/123 |
| 584271 | 2/1925 | France | 239/45 |

Primary Examiner—Barry S. Richman
Attorney, Agent, or Firm—Hayes, Davis & Soloway

[57] ABSTRACT

A vapor dispersing device in which evaporative dispersion of volatile and diffusive components of an air treating agent is regulated over an extending period by the use of a container, for the agent, into which at least one rigid porous wick extends to transfer the agent from the container to a porous plastic element from the surface of which dispersion of the agent will occur by means of evaporation, the surface of the element being impregnated with an occluding agent, the evaporation rate of which is chosen, relative to rate of deposition on nonvolatile components of the air treating agent in the element, to result in an even dispersion rate over a desired operating period.

7 Claims, 1 Drawing Figure

U.S. Patent     Nov. 8, 1983     4,413,779
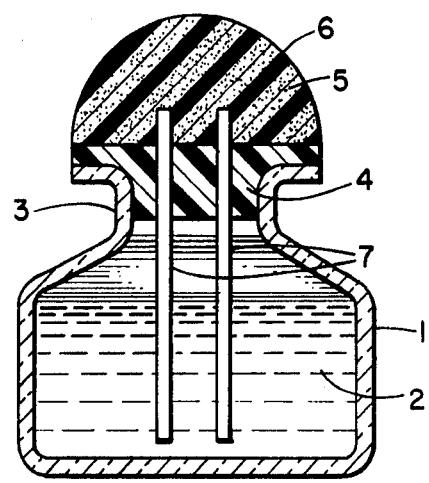

VAPOR DISPERSING DEVICE

This application is a continuation-in-part of U.S. patent application Ser. No. 246,089 filed Mar. 23, 1981, now abandoned.

The present invention relates to a vapor dispersing device and process for volatile materials or agents for deodorizers, fragrances, insecticides, decongestants and the like. In particular, though not exclusively the invention relates to such devices and processes in which the rate of dispersion is substantially even over an extended period of time.

There have been numerous methods devised which attempt to regulate the diffusion rate of these volatile materials especially with regards to the fragrancing and deodorization of an enclosed room. Prior art devices which relate to this area are disclosed in U.S. Pat. Nos.: 525,646; 1,123,036; 1,129,897; 2,507,889; 2,616,759; 2,657,090; 2,787,496; 2,797,844; 2,878,060; 2,961,167; 2,975,464; 3,104,816; 3,239,145; 3,550,853; 3,633,881; 3,679,133; 3,804,331; 4,014,501; 4,094,639; and in French Pat. No. 584.271. The primary function of these types of devices for commercial use has been in the area of deodorization and the counteractancy of malodors. As the stress begins to change, however, from the dispensing of fragrance compounds which are meant to mask malodors to the controlled release of fine fragrance solely for the aesthetic appeal that these materials generate, then it is clear that the prior art devices are not well suited to this function.

Although it is reasonable to imagine that it is within the scope of the present art to devise an apparatus which is capable of exerting some measure of control over the diffusion rate of a volatile material, the current devices whether they are of the continuous element type of wicking mechanism (Air-Wick) or a device which uses a wick integral with an absorbent element (U.S. Pat. No. 2,975,464) in fact offer little governance nor propose to offer control over the rate at which diffusion takes place. The rate is roughly established as a function of the amount of surface which is exposed on the part of the absorbent diffusing element. This element normally operates from a state of saturation from its either being the wick or because of its contact with the wick. The option of varying the size of the components used in these devices certainly gives them a broader range of application than can be found in their ability to govern their rates of diffusion from any inherent design feature. The claim could be made that unstoppered bottles containing volatile materials represent a form of vapor diffusing device and that as the size of the bottle opening was varied so too would you see a difference in the diffusion rate. None of the devices embodied in the prior art possesses a design which contributes to a performance which is likely to make them much more effective than a device which functions on a principle as basic as an unattended opened bottle.

Another duplication of their performance might also be achieved by the use of a container fitted with a porous, absorbent element which would become saturated when the container was inverted. This would not differ greatly from their present method of use and is even a suggested mode of operation for the container described in U.S. Pat. No. 2,975,464. The point made by these examples is that just as the current devices were once protected by patent coverage because of their extension of a rather basic art, so too does the device we disclose represent an advance over what is currently known in this area. The ability to produce a controlled vapor diffusing device whose full range of performance cannot be duplicated by any other single device underlies our belief that in fact we are extending the art through disclosure of this unit.

With respect to U.S. Pat. No. 2,975,464 it is to be noted that the container which is the subject of this patent is for dispensing liquid in the manner of an applicator for the liquid, for example, to dispense a liquid shoe polish. There is no suggestion in this patent that the construction disclosed would be suitable for dispensing volatile materials by evaporation into the atmosphere and, further there is no suggestion in that the rate of such dispensation might be appropriately controlled and extended.

The ability for a single static vapor diffusing device to uniformly regulate the rate of release of air-treating agents was also the subject of my prior patent application Ser. No. 137,022 filed Apr. 3, 1980, now abandoned. This device was composed, in a preferred form, of a porous plastic diffusion element or elements connected to a liquid reservoir of air-treating materials through rigid plastic wicking rods. The ability to design into this device a dispersion rate of desired proportions was a fundamental aspect of this disclosed technology. The regulatory nature of this device was achieved through the selection of a diffusion element of a particular size, porosity and surface area to be used in conjunction with a wicking system in which the liquid composition being transported out of the container was made available to the diffusion element at a rate influenced by the size and number of transport wicks and/or by the exposed area of an adjustable diffusion element or elements.

Commercially available devices designed for this same function utilize a continuous strip of a cellulosic fabric which serves as both the diffusion element and the wick. These devices are able to provide a consistent rate of release primarily through the use of liquid fragrance compositions consisting of fragrance and volatile diluting carriers which result in solutions whose non-volatile components are kept at functional minimums (i.e. less than 2%). This is in direct contrast to the type of air-treating compositions cited in the previous disclosure and in accordance with the present invention. Wherein fragrance compositions consisting of fragrance, volatile carriers and solubilizing agents with non-volatile concentrations as high as 30% by weight, although 15–20% is preferred, are practical.

The advantage of a device which continuously replenishes the diffusion element with fresh fragrance and which in its fabrication does not subject the fragrance to harmful processing environments signals an important advantage over other devices designed for air-treatment and deodorization. This can be attributed to the fact that the most volatile and fugitive components of the fragrance which are often those most easily perceived olfactively are not prematurely lost and as a result are available for dispensing throughout the life of the device.

The numerous approaches which have been used in an attempt to diffuse a continuous or semi-continuous level of air-treating materials in a closed or substantially closed space include gels, paper blotters, polymer and wax type units. All of these attempts are limited either by their inability to offer any substantial degree of sustained fragrance release or due to fabrication requirements (e.g. heat and chemical) which have a damaging effect upon the original fragrance quality and character. It is often the case that specialty compounded fragrances which are less susceptible to heat or chemical processing are used in those instances when these processing parameters are likely to be encountered to minimize the potential for instability under these conditions.

These shortcomings are not a problem with either the device of my patent application Ser. No. 137,022 or with the present invention. The result is a dispenser which is suited for use with a broader range of fragrance types and air-treating agents than can currently be effectively used in the prior art, including commercially available units. The present invention seeks to substantially improve the performance potential of devices such as are disclosed in the prior application.

The problem inherent in dispensing fragrance solutions or compositions (all references herein to fragrance solutions/compositions is meant to include not only the fragrance oil, but the entire solution consisting also of volatile diluting carriers and surface active solubilizing agents) with non-volatile fractions as high as 30% is that the residual components in these compositions come ultimately to reside in the diffusion element. The increasing concentration of these materials in the diffusion element over a period of time inevitably results in a diminished efficiency due to the decrease in available surface from which evaporation can take place. This process has an adverse effect on the ability of the device to maintain a constant rate of release since this rate is a direct function of the surface available at any of the interfaces which exist between the porous diffusion element and the surrounding atmosphere.

It has been the practice of the currently available commercial wicking type of air-treating devices to exert control over the delivery rate by basically utilizing two techniques, namely the option of using (a) fragrance compositions which contain low concentrations of residual components or (b) using a diffusion element of such size that any reduced surface offers little to no retarding effects on the established delivery rate. With respect to the first of these techniques an evaluation showed a non-volatile fraction ranging in the order of between 1.0% and 1.5% in commercially available liquid fragrance solutions.

The problem associated in dispensing fragrance compositions is fixed element vapor dispersing devices with non-volatile fractions as high as those cited in accordance with the present invention is a significantly different problem than that addressed by anything in the prior art or represented by commercially available units.

Although a consistent release rate over a short period for a given fragrance composition can be established experimentally in a vapor dispersing device employing a fixed diffusion element, the maintenance of this rate over a reasonable period of time has proven difficult. The diminishing efficiency which results in the diffusion element as a function of the increasing concentration of non-volatile materials which come to reside in this element is essentially the source of this difficulty. Any experimentally established rates which might prove satisfactory in the early stages of the units functional life usually decrease and become inadequate in its latter stages of operation.

It is, accordingly, an object of the present invention to provide a device for volatile materials which can be easily modified to offer control over the rate of diffusion through a porous diffusion element impregnated with an occluding agent.

It is a further object of the present invention to present a device which uniformly dispenses a liquid air-treating composition containing as high as 30% non-volatile components in an efficient and economical manner for a reasonable period of time, which can be prepared in a variety of sizes so that the non-volatile content of the fragrance composition and the duration of time for which it is intended to function is a matter of choice on the part of the manufacturer. Certainly functional periods of from one to eight weeks are within the effective range of this device.

It is the intention of this disclosure to present a novel method using chemical agents to provide for a vapor diffusing process such that a sustained, controlled vapor release will result. The device and methodology in accordance with the present invention relates to the use of volatile chemical agents either used alone or in combination and in particular, though not exclusively, to the use of volatile hydrocarbon solvents of the isoparaffinic and normal paraffinic type for use as non-permanent occluding agents in fixed element vapor dispersing devices.

According to one aspect the invention provides a vapor dispersing device comprising a porous element having an open cell surface impregnated with a volatile occluding agent.

According to another aspect the invention provides a vapor dispersion process comprising impregnating a porous element having an open cell surface with a volatile occluding agent, and then supplying a liquid, having volatile and non-volatile components, to element for evaporative dispersion from the surface.

This invention involves a process whereby the diffusion element of the device is impregnated with a single volatile material or a combination of volatile materials such that the rate of evaporation of this solvent from the diffusion element approximates the rate of occlusion occurring as a result of the deposition of non-volatile components from the fragrance solution. The continuing availability of newly exposed surface made available by the evaporation of the volatile retardant solvent or solvents and the continuing occlusion by the residual components of the solution being dispensed results in an equilibrium whereby the rate of material dispensed over a given period of time should be relatively even due to the constancy of surface available for diffusion.

This invention will now be described, by way of example, with reference to the accompanying drawing, which is a diagrammatic sectional elevation of a device according to the invention.

With reference to the invention as illustrated in the drawing a glass container 1 which in use will contain a fluid 2 to be dispensed by evaporation. An upwardly facing opening of the container is defined by a neck 3 in which is located a tightly fitting stopper 4 to the upper surface of which is attached a rigid plastic porous element 5 defining a hemispherical open cell surface 6. Two rigid porous nylon wicks 7 extend from adjacent the lower extremity of the container 1 below the level of the liquid 2 and through the stopper 4 into contact with the element 5.

It will be appreciated that the pressure in the container will be maintained at or slightly above ambient pressure. This, for example, may be achieved by permitting sufficient air to pass the stopper 4 to achieve pressure balance or by the use of a liquid to be dispensed, or an additive thereto or a component thereof, the volatility of which is sufficient to produce a vapor pressure within the container to maintain or exceed ambient pressure. The passage of air, for example, may be achieved by the use of a wicking element passing through the stopper, passages through the stopper or other air communicating means passing from the exterior of the device to the space above the liquid in the container. Preferably this passage is controlled by pore size, material choice, capillary size, membrane structure, or any combination of these, to selectively allow air to enter the container while preventing liquid from passing out of the container.

The element 5 is constructed from a rigid porous polyethylene material with a uniform controlled pore structure which defines an open cell smooth surface 6, for example, the plastic sold under the trademark "Interflow" of Chromex Chemical Corporation. The wicks 7 are a nylon fiber mass of continuous filaments bonded together to form an integral element having a porosity to promote a wicking action. The element 5 is impregnated with a volatile occluding agent.

The characteristics of the porosity of the element 5, the occluding agent and the diameter and porosity of the wick 7 is chosen in dependence upon the fluid to be dispensed with reference to its evaporation rate, the desired rate of dispensation and the pore clogging characteristics of non-volatile or relatively less-volatile components of the fluid to be dispensed.

In use a fluid to be dispensed which may be a deodorizing fluid, is wicked by wick 7 to the rigid porous elements 5 and is conducted thereby to the hemispherical surface 6 where the fluid is dispensed by evaporation into the surrounding atmosphere.

As the non-volatile components of the fluid dispersed progressively clog the pores of the element 5, the occluding agent evaporates to maintain a desired area of dispersing surface in order to provide a substantially contant rate of dispersation of the fluid.

It will be appreciated that the invention is not restricted to devices with a fixed area of exposed surface and that various methods of adjusting the area of the exposed surface of the rigid plastic porous element may be employed, for example, those described in the second, third, and fourth embodiments of the invention disclosed in applicant's copending U.S. patent application Ser. No. 137,022.

It will also be appreciated that while the porous element has been described as a rigid plastic material, other materials, which may not be plastic, will be appropriate for use providing their porosity and open cell surface fulfills the requirements for evaporation of the liquid to be dispensed therefrom.

The preferred choice for volatile occluding agents is not limited to the isoparaffinic or normal paraffinic solvents, however, they represent the group of choice for use in this application for four important reasons:

(1) Inhalation Toxicology—In a device of this type whose intended purpose is likely to bring it in repeated contact with people under confined condition, the concern for finding a volatile occluding agent which poses the least possible risk with regards to inhalation toxicology is important. Whereas there might be a number of volatile chemical materials available to duplicate the performance of the isoparaffinic and normal paraffinic solvents (e.g. glycol ethers of the "Cellosolve", "Carbitol", and "Propasol" type-Union Carbide) these and similar solvents because of their suspected toxicological properties makes them undesirable for use in a device designed for this purpose.

(2) Odor—Since the primary function of this device is to create a pleasant olfactory environment any choice of a volatile retarding chemical composition should reflect this end use. Although the use of solvents with unpleasant odors is counterproductive for use in air deodorizing devices, they might, however, be suited for use in devices designed for the dispensing of active air-treating agents such as those used for insecticidal materials. The isoparaffinic and normal paraffinic type solvents typically have a very mild unobjectionable odor and good odor stability which makes them especially well suited for this purpose.

(3) Range of Volatility—Ideally, the preferred class of volatile chemical retarding agents should offer materials which provide access to a broad range of vapor pressures. In this way by varying both the proportions in which these materials might be used in combination with one another and by varying the load level for a particular device considerable flexibility can be achieved with regards to altering the performance of a device. Therefore, any variations in the evaporative rate of the fragrance compositions or changes in the length of the products functional life could easily be adapted for without changing any of the integral parts used in the fabrication of the device. The isoparaffinic and normal paraffinic hydrocarbon solvents represent materials which offer this full range of volatilites and makes them easily suited for this application. These petroleum distillates as well as any volatile fractions synthesized from petroleum derived raw materials of these general types are manufactured under various commercial trade names to include: Isopar and Norpar (Exxon Company), Soltrol (Phillips Petroleum) and Shell Sol (Shell Chemical). A survey of the available Isopar and Norpar hydrocarbon fractions show that there are seven different isoparaffinic type solvents and two normal paraffinic type solvents offered. The boiling range and the 50% volume evaporation loss as measured by a modified Wetlaufer-Gregor method and as recorded in the Exxon Petroleum Solvent Handbook (Lubetext DG-1P) for these solvents is recorded below:

| Commercial Name | Solvent Type | Boiling Range | 50% Volume Evaporation Rate |
| --- | --- | --- | --- |
| Isopar C | Isoparaffinic | 90–106° C. | 141 Seconds |
| Isopar E | Isoparaffinic | 116–139° C. | 360 Seconds |
| Isopar G | Isoparaffinic | 157–176° C. | 2,700 seconds |
| Isopar H | Isoparaffinic | 176–191° C. | 5,900 seconds |
| Isopar K | Isoparaffinic | 177–197° C. | 6,200 seconds |
| Isopar L | Isoparaffinic | Mid-range 194° C. | 12,000 seconds |
| Isopar M | Isoparaffinic | 207–254° C. | 32,400 seconds |
| Norpar 12 | normal-paraffinic | 188–219° C. | 22,800 seconds |
| Norpar 13 | normal-paraffinic | 228–248° C. | not available |

As indicated by this chart the availability of this large number of solvent fractions with their differing volatilities makes these materials especially useful from which to select either a single or combination of materials for use as non-permanent volatile occluding agents.

(4) Cost—The economical aspects of using these types of volatile agents is extremely favorable since these fractions represent some of the least expensive of the petroleum derived solvents. Their use therefore would not likely be precluded due to any cost differential versus any other type of volatile material.

Although the isoparaffinic and normal paraffinic solvents remain the preferred group for the reasons previously stated, this does not preclude the potential use of virtually any volatile liquid, combination of liquids or liquid solutions of dissolved solids whose performance proves satisfactory within the criteria established by the fabricator. The choice of using an alternate occluding agent is ultimately a matter to be evaluated within a framework defined by the end use of the device, its size, the evaporative rate of the solution being dispensed and the functional life expected from the unit. An example of some representative chemical compounds from a broad range of chemical groups which might contain materials useful for this application and common to the art would be: alcohols such as ethanol, propanol, isopropanol, butanol, aliphatics such as hexane, heptane, mineral spirits, amines such as morpholine, butylamine, chlorinated hydrocarbons such as perchlorethylene, esters such as methyl amyl acetate, n-butyl acetate, glycol ethers such as ethylene glycol methyl ether, ketones such as diisobutyl ketone, silicones such as polydimethyl cyclosiloxane and miscellaneous solvents such as water and 2-nitropropane.

Two points should be noted: (1) none of the compounds in the above list satisfies the four point criteria as completely as do the isoparaffinic or normal paraffinic hydrocarbon fractions; (2) those materials which are listed and are of an extremely volatile nature (e.g. ethanol, hexane, perchlorethylene) offer little retardancy in the long term due to their fugitive nature. However, depending on the nature of the composition being dispensed they might under certain circumstances prove useful and for that reason have been included.

To illustrate the ability of the disclosed method to uniformly regulate the release of a fragrance composition the following tests were conducted.

EXAMPLE I

Two identical vapor diffusing devices were prepared using the same type of porous plastic diffusion element manufactured by the Chromex Chemical Company weighing three (3) grams and having a volume of 0.54 in.$^3$. These diffusion elements having the shape of a conical section were interconnected to the liquid fragrance reservoir with a rigid nylon wicking rod manufactured by the American Filtrona Company (Transwick No. R-8078) and having a diameter of 0.078 in. The fragrance solution, used in this experiment is disclosed below and included is also the compositional formula for the fragrance oil used:

| Ingredient | Parts by Weight |
|---|---|
| FRAGRANCE SOLUTION | |
| Water | 55.0 |
| Ethanol | 30.0 |
| Nonoxynol-9 (GAF Corp.-Igepal CO-630) | 5.0 |
| Nonoxynol-30 (GAF Corp.-Igepal CO-880) | 2.0 |
| Fragrance Oil (Hyacinth type) | 8.0 |
| | 100.0 |
| FRAGRANCE OIL (HYACINTH TYPE) | |
| Phenylethyl Alcohol | 40.0 |
| Benzyl Acetate | 10.0 |
| Benzyl Salicylate | 12.0 |
| d-limonene | 10.0 |
| Phenylacetaldehyde dimethylacetal | 4.0 |
| Terpineol | 1.5 |
| Hydroxycitronellal | 6.0 |
| Eugenol | 2.4 |
| Dipropylene Glycol | 14.1 |
| | 100.0 |

This fragrance solution cited has a residual, non-volatile fraction of 14.2% as measured gravimetrically to a constant weight under ambient conditions (22° C). This number is a result of the non-volatile nature of both nonoxynol surface active agents as well as the contribution made by the non-volatile components of the fragrance whose composition is also disclosed. The unit in accordance with the present invention was prepared by first impregnating the porous plastic diffusion element with 2.0 g. of Isopar M (Exxon) prior to its being connected to the liquid reservoir through its engagement with the rigid wicking element. The other and a control unit was prepared using identical components, however, no retarding solvent was used on the diffusion element. Both units were allowed to stand under ambient conditions and the weight losses recorded at a period of every three days for a total duration of three weeks. The period weight loss results and their deviation from an ideal value which would reflect the weight loss per period for dispensing the same amount of fragrance solution if a totally uniform dispensing rate were achieved is also included and cited in each of the tables of recorded data. Table I represents that information recorded for the unit in accordance with the present invention in which a volatile occluding agent was utilized.

TABLE I

| Period | Days | Weight Loss Per Period (Grams) | Ideal Average Weight Loss (Grams) | % Variance in Weight Loss Per Period from Ideal Average Period Weight Loss |
|---|---|---|---|---|
| 1 | 0–3 | 2.81 | 2.66 | +5.6% |
| 2 | 4–6 | 2.57 | 2.66 | −3.4% |
| 3 | 7–9 | 2.51 | 2.66 | −5.6% |
| 4 | 10–12 | 2.65 | 2.66 | −0.4% |
| 5 | 13–15 | 2.62 | 2.66 | −1.5% |
| 6 | 16–18 | 2.82 | 2.66 | +6.0% |
| 7 | 19–21 | 2.64 | 2.66 | −0.8% |
| Total | | 18.62 g. | 18.62 g. | |

$$\%\text{ Variance in Weight Loss per Period from Ideal Average Period Weight Loss} = 100 \times \frac{\text{Weight Loss per period} - \frac{\text{Total Weight Loss}}{\text{Number of Periods}}}{\frac{\text{Total Weight Loss}}{\text{Number of Periods}}}$$

In contradistinction to this regulated release the identical device prepared without using a retarding solvent was allowed to stand under the same conditions as the previous device. The results of this test are set forth in Table II.

TABLE II

| Period | Days | Weight Loss Per Period (Grams) | Ideal Average Weight Loss (Grams) | % Variance in Weight Loss Per Period from Ideal Average Period Weight Loss |
|---|---|---|---|---|
| 1 | 0–3 | 11.45 | 3.60 | +218.1% |
| 2 | 4–6 | 5.78 | 3.60 | +60.6% |
| 3 | 7–9 | 3.18 | 3.60 | −11.7% |
| 4 | 10–12 | 2.08 | 3.60 | −42.2% |
| 5 | 13–15 | 1.17 | 3.60 | −67.5% |
| 6 | 16–18 | 0.87 | 3.60 | −75.8% |
| 7 | 19–21 | 0.65 | 3.60 | −81.9% |
|   | Total | 25.18 | 25.20 |   |

It is readily apparent from a comparison of the above two tables that the device which utilized a diffusion element which was impregnated with the volatile occluding agent exhibited an evaporation rate which was significantly more regulated and uniform than the control device. The comparison of the two units showed that the device in accordance with the present invention deviated from the ideal average period weight loss during the seven period twnenty-one day test ranging from a high of 6.0% to a low 0.4%. This is in contrast to the control device which showed a deviation from the ideal average period weight loss ranging from a high of 218.1% to a low of 11.7%.

EXAMPLE II

Two vapor dispersing devices were prepared in accordance with the components as described in Example I. The test solution whose compositional formula is disclosed below had a non-volatile content of 1.75%.

Fragrance Solution Formula (High Volatility)

| Ingredient | % w/w |
|---|---|
| Water | 58.0 |
| Ethanol | 40.0 |
| Nonoxynol-9 (GAF Corporation-Igepal CO-630) | 0.5 |
| Nonoxynol-30 (GAF Corporation-Igepal CO-880) | 0.5 |
| Fragrance (Hyacinth Type) | 1.0 |
|  | 100.0 |

One device was prepared as a control while the other device (Unit 1) was prepared using 3.1 grams of a solution of 95 parts Isopar M and 5 parts Isopar K applied to the diffusion element prior to its connection with the wick and fragrance reservoir. In spite of the extremely volatile nature of the fragrance solution being used in this experiment the presence of non-volatile components even at a level of 1.75% is capable of producing a change in the release rate of a fixed element vapor dispersing device. The use of a volatile occluding agent as applied in accordance with the methodology disclosed should serve in this instance to provide a more uniform and regulated release than that which results from the control unit. Table I illustrates the difference in the performance of these two units through a comparison of their relative dispensing characteristics as measured during an eight (8) day test.

TABLE I

| Device | Total Wt. Lost 8 days (grams) | Period 1 Wt. Lost Days 0–4 (grams) | Period 2 Wt. Lost Days 4–8 (grams) | (Period 1) − (Period 2) (grams) |
|---|---|---|---|---|
| Control | 58.88 | 31.41 | 27.47 | +3.94 |
| Unit 1 | 36.22 | 17.65 | 18.57 | −0.92 |

The diminished release evident in the control device during period 2 is expected based on the increasing concentration of residual components in the diffusion element. In contrast, however, Unit 1, which utilizes the volatile occluding solvent demonstrates a different behavior by showing an overall smaller magnitude of release as well as a higher weight loss during period 2 than period 1. This is indicative of a situation in which the choice of occluding agent in combination with loading used has a greater influence over the rate and magnitude of release than does the nature of the solution being dispensed. The evaporation rate of the retarding solvent in this particular case has exceeded the rate of occluding caused by the accumulation of non-volatile agents from the solution being dispensed. This has created a situation whereby there was slightly more surface available for evaporation in the latter half of this test than was available during the first half. This situation could be remedied by altering the load level, or choice of volatile occluding materials in tests to arrive at the correct experimentally derived values for these variables.

EXAMPLE III

Example III was performed in a manner similar to that described in previous example I and example II. One unit was prepared as a control while the other device (Unit II) was prepared using a diffusion element that was impregnated with 3.67 grams of Isopar M prior to its connection with the wick and fragrance reservoir. The test solution whose compositional formula is disclosed below had a non-volatile content of 29.6%.

Fragrance Solution Formula (Low Volatility)

| Ingredient | % w/w |
|---|---|
| Water | 27.0 |
| Ethanol | 40.0 |
| Nonoxynol-9 (GAF Corporation-Igepal CO-630) | 3.0 |
| Fragrance (Hyacinth type) | 30.0 |
|  | 100.0 |

Table II illustrates the difference in the performance of these two devices through a comparison of their relative dispensing characteristics as measured during an eight (8) day test.

TABLE II

| Device | Total Wt. Lost 8 days (grams) | Period 1 Wt. Lost Days 0–4 (grams) | Period 2 Wt. Lost Days 4–8 (grams) | (Period 1) − (Period 2) (grams) |
|---|---|---|---|---|
| Control | 12.55 | 10.70 | 1.85 | +8.85 |
| Unit II | 6.18 | 3.14 | 3.04 | +0.10 |

It is readily apparent from this above data that the use of a volatile occluding agent provided a significant influence over the magnitude and uniformity at which the fragrance solution was diffused out of this device. A comparison of examples I, II and III demonstrates that the use of this disclosed technology provides a much more significant contrast against a control when the solution being dispensed has a greater clogging potential as is the case in example III which uses a solution with a significantly higher residual content than that of example I. This is consistent with the fact that the disclosed methodology was developed specifically to offset the effect the residual components of the solution being dispensed had on the available surface of the diffusion element and its resultant effect on evaporation.

It is evident based on this comparison that the treatment of the diffusion element prior to its engagement with the liquid reservoir with an experimentally derived loading of volatile occluding agents provides a quality of performance that was unattainable in the control unit. The degree of regulation that can be achieved in the release rate and concurrent fragrance evaporation in a fixed element vapor dispersing device through the utilization of this presently disclosed technology provides a mechanism for the use of a larger selection of fragrance types in more concentrated and compact devices than can now be achieved using technology representing the current art.

I claim:

1. A vapor dispersing device comprising a porous element having an open cell surface, and means for supplying to said surface an air treating liquid which has volatile and non-volatile components, said non-volatile component having a predetermined occluding rate on said open cell surface when said liquid evaporates therefrom, said open cell surface being initially impregnated, prior to supply of said liquid thereto, with an occluding agent which has a desired evaporation rate having a desired relation to said predetermined occluding rate, thereby to provide a desired evaporation rate of said liquid from said surface over an extended period of time.

2. A vapor dispersing device according to claim 1 wherein said means is a container having an opening, a wick extending from an outer end thereof through the opening into the container and said element is disposed for communication with the outer end of the wick to receive liquid wicked from the container.

3. A vapor dispersing device according to claim 1 wherein the occluding agent is chosen from the group comprising isoparaffinic or normal paraffinic solvents.

4. A vapor dispersion device according to claim 1 wherein the element is a rigid porous plastic material.

5. A vapor dispersing device comprising a porous element having an open cell surface, and means for supplying to said surface an an air treating liquid which has volatile and non-volatile components, said non-volatile component having a predetermined occluding rate on said open cell surface when said liquid evaporates therefrom, said open cell surface being initially impregnated, prior to supply of said liquid thereto, with an occluding agent which has a desired evaporation rate substantially matching said predetermined occluding rate, whereby the evaporation rate of said liquid from said surface is maintained essentially constant over an extended period of time.

6. A vapor dispersing device according to claim 5 wherein the liquid includes up to 30% by weight of non-volatile components.

7. A vapor dispersing device according to claim 6 wherein the liquid includes more than 2% by weight of non-volatile components.

* * * * *